United States Patent
Osada et al.

(10) Patent No.: US 6,782,733 B2
(45) Date of Patent: Aug. 31, 2004

(54) METHOD FOR ESTIMATING THE CHANGE OF BODY SMELL WITH AGEING

(75) Inventors: Kazumi Osada, Bryn Mawr, PA (US); Kunio Yamazaki, Havertown, PA (US); Gary K. Beauchamp, Philadelphia, PA (US)

(73) Assignees: Taisho Pharmaceutical Co. Ltd., Tokyo (JP); Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 10/223,437

(22) Filed: Aug. 20, 2002

(65) Prior Publication Data

US 2003/0033853 A1 Feb. 20, 2003

Related U.S. Application Data

(60) Provisional application No. 60/313,013, filed on Aug. 20, 2001.

(51) Int. Cl.$^7$ ............................................. G01N 33/483
(52) U.S. Cl. ........................ 73/23.34; 73/23.2; 73/23.35
(58) Field of Search ............................. 73/23.35, 23.34, 73/23.3, 23.2, 23.22; 422/84, 89, 70

(56) References Cited

U.S. PATENT DOCUMENTS

| | | | |
|---|---|---|---|
| 6,129,680 A | * | 10/2000 | Mottram ..................... 600/532 |
| 6,248,078 B1 | * | 6/2001 | Risby et al. ................. 600/529 |
| 6,411,905 B1 | * | 6/2002 | Guoliang et al. ............. 702/23 |
| 6,461,306 B1 | * | 10/2002 | Hanson, III et al. ......... 600/532 |
| 6,497,862 B2 | * | 12/2002 | Oku et al. .................... 424/65 |
| 6,526,806 B2 | * | 3/2003 | Kuttenberger ............... 73/23.3 |
| 6,631,333 B1 | * | 10/2003 | Lewis et al. .................. 702/24 |

FOREIGN PATENT DOCUMENTS

EP        0 955 035 A1    11/1999

OTHER PUBLICATIONS

Shinichiro Haze, et al., "2–Nonenal Newly Found in Human Body Odor Tends to Increase with Aging," J. Invest. Dermatol., Apr. 2001, pp. 520–524, vol. 116, No. 4.

Alan G. Singer, et al., "Volatile signals of the major histocompatibility complex in male mouse urine," Proc. Natl. Acad. Sci. USA, Biochemistry, Mar. 1997, pp. 2210–2214, vol. 94.

M. Ayasse, et al., "Ontogenetic patterns of volatiles identified in Dufour's gland extracts from queens and workers of the primitively eusocial halictine bee, Lasioglossum malachurum (Hymenopters: Halicidae)," Insectes Sociaux, 1993, pp. 41–58, vol. 40, No. 1, (abstract only).

* cited by examiner

*Primary Examiner*—Hezron Williams
*Assistant Examiner*—Rodney Frank
(74) *Attorney, Agent, or Firm*—Sughrue Mion, PLLC

(57) ABSTRACT

It is desirable to provide a gas chromatography type of chemical analysis method for estimating the change of body smell with progressive ageing of a living subject over a period of years by 1) utilization of the smell distinguishing ability of an experimental animal, 2) instrumental analysis, or 3) a combination of them.

The present inventors found that the amounts of several volatile organic substances (e.g., 2-phenylacetamide, indole and phenol) present in mouse urine as substances responsible for the body smell are increased or decreased with ageing. The change in body smell with ageing of an animal can be estimated by quantitatively analyzing these compounds by an instrumental analysis method such as Y-shaped labyrinth method (involving live animals in a maze), gas chromatograph (GC) or high performance liquid chromatography (HPLC).

3 Claims, No Drawings

METHOD FOR ESTIMATING THE CHANGE OF BODY SMELL WITH AGEING

This application claims benefit from Provisional Application No. 60/313,013 filed Aug. 20, 2001, the disclosure of which is incorporated herein by reference.

DISCLOSURE OF THE INVENTION

This invention relates to a method for detecting a smell-emitting substance produced owing to ageing, by using Y-shaped labyrinth or GC.

Experimental Animals and Method for Collecting Urine

Mice (C57BL/6J-H-2-k) were used as smell sensors (n=5) for Y-shaped labyrinth and as experimental animals for estimating the change of the body smell with ageing. The mice were divided into three groups (n=15–30), i.e., a group of young mice (1–3 months), a group of adult mice (3–10 months) and a group of aged mice (>17 months). Urine was used as a smell source. Urine was collected from each group by lightly pressing the bladders of the mice so as to minimize a stress imposed to the mice. Each urine sample is a mixture of urines collected from 2 to 6 mice in the same group. Each sample was stored at −20° C.

Preparation of Samples for Y-shaped Labyrinth Method and Gas Chromatography

Ether extract fractions of the urine samples were/prepared according to the method described in reference 1. Each urine sample was subjected to centrifugal filtration at 5° C. and 5,000×g (6,500 rpm) by the use of Centricon-10 (Amicon, 10,000 MW cut off) to remove urinary proteins such as major urinary proteins. Then, 1.0 ml of the filtered urine sample was saturated with 200 mg of $KH_2PO_4$ to obtain a weekly acidic fluid (pH 4.4–4.6). This fluid was extracted by shaking for 2 hours with diethyl ether (HPLC grade) 15 times volume as much as the fluid. The extract solution was dispensed in 7.5-ml aliquots into test tubes, after which the extract solution in each tube was concentrated to 0.5 ml with Speed Vac (60 min) and freeze-dried for about 70 minutes.

Y-shaped Labyrinth Method (Involving Live Animals in a Maze)

The change of the body smell with ageing was estimated by Y-shaped labyrinth method according to the method described in reference 2. FIG. 1 shows a general view of Y-shaped labyrinth. In Y-shaped labyrinth method, a urine sample is placed in a box located at an end of the two branches of the Y-shaped labyrinth, and another urine sample is placed in the other box located at the other end of the two branches of the Y-shaped labyrinth. The two urine samples are from two groups of mice that belong to the same strain but are at different ages. The mice are trained to select the smell of one of the urine samples. The mice have been fed with a sufficient diet but have been given a limited volume of water. They are given a drop of water as a reward only when they select the correct smell. If the mice can distinguish the smells, this discrimination proves that the smell given out by the animal varies depending on the age of the animal. Although the percentage of correct answers by the trained mice is about 50% for first several days, it increases gradually and exceeds 80%. In the present example, the mice were trained at first to distinguish the 5-fold dilutions of urine samples of the group of adult mice from those of the group of aged mice. Then, whether the mice could distinguish the ether extracts of urine samples was confirmed. Lastly, whether the mice could distinguish the ether extracts of different urine samples without being rewarded with water was observed.

Conditions of Gas Chromatography

Gas chromatography was carried out by using Varian 3300. In the experiments, a Stabilwax column (30 m×0.32 mm i.d.·10 μm df) was used as a column for separation after having been equipped with a 5 m×0.53 mm i.d. guard column (Restek, Bellefonte, Pa.). Solutions prepared by re-dissolving the ether extract of the weekly acidic urine in methyl acetate were used as samples as described above. Fractions composed mainly of any of volatile organic acids, amines, amides and the like in the urine samples from the mice were identified. The column temperature was maintained at 80° C. for 2 minutes and then raised to 240° C. at a rate of 5° C. per minute. Helium was used as a carrier gas and the linear velocity was adjusted to 37 cm/sec (at a column temperature of 40° C.). Quantitative analysis of the components on the chromatogram was conducted according to peak percentage method.

RESULTS AND CONSIDERATION

As a result of the discrimination experiment using the Y-shaped labyrinth, the smell sensor mice trained to distinguish the components which are responsible for the body smell and contained in the urine samples from the aged and adult mice showed a discrimination rate in the 5-fold diluted urine samples of 82% ($p<0.001$; number of trials 60), whereas they showed a high discrimination rate in the ether extracts of urine samples of 91% ($p<0.001$; number of trials 73). They showed a high discrimination rate of 84% ($p<0.001$; number of trials 25) also in the generalization test involving no rewarding. These results prove that substances responsible for the body smell which change with ageing are contained in the ether extracts of the urine samples (FIG. 2).

FIG. 3 shows gas chromatograms obtained for the ether extracts of urine samples from the group of young mice, the group of adult mice and the group of aged mice. Table 1 is a list of compounds, of which the structures are determined by GC-MS.

A large number of peaks assigned to various substances were confirmed in the gas chromatograms obtained for the ether extracts, but no such compound could be found as was specific to any one of the age groups. This fact indicates that the change of the body smell with ageing is not caused by the appearance of a specific and single substance. However, of the compounds corresponding to the 38 peaks observed by us, five compounds were significantly increased in amount in the group of aged mice and three compounds are decreased in amount in the group of aged mice, as compared with the group of young mice and the group of adult mice (Table 1).

Of these compounds, the compounds that were increased in amounts with ageing can be considered the main substances responsible for senile smell. Of such compounds, those having a known structure are the following four compounds: 2-phenylacetamide (No. 34), indole (No. 25), phenol (No. 13) and cedrene (No. 3). Five compounds, i.e., the above four compounds and an unknown compound of No. 26 (see Table 1) that appears at a retention time of each gas chromatogram of about 31 minutes, are the compounds produced in large amounts specifically in the aged animals. On the other hand, the following three compounds were decreased in amounts with ageing: No. 6 (methyl butyric acid), No. 31 (unknown) and No. 32 (unknown).

2-Phenylacetamide, a metabolite of phenylalanine, is a precursor of phenylacetic acid. The amount of phenylacetic acid discharged into body fluids is strictly defined depending on the difference in haplotype of MHC class I molecule (see reference 1). In addition, an investigation using mice deficient in MHC class I has revealed that the appearance of MHC class I at cell surface is required for the formation of a normal smelling type (see reference 3). An experiment using a Y-shaped labyrinth has revealed that in the case of mice deficient in MHC class I, the change in body smell of the mice with ageing is difficult to be detected (the experimental data have not yet been published). These facts suggest the possibility that 2-phenylacetamide can be a substance responsible for senile smell which reflects the change of immunological functions with ageing.

Indole, a metabolite of tryptophan, is probably a substance produced by a flora in alimentary canal. Therefore, this substance responsible for senile smell can reflect the change of an intestinal flora with ageing or the change in function of alimentary canal with ageing. It is conjectured that cedrene was accumulated in the body of the mice owing to their living environment such as bedding.

Measurement of the change in the content(s) of one or more of such compounds permits estimation of the change in the body smell with ageing.

REFERENCES

1) Singer, A., Beauchamp. G. K. & Yamazaki, K. (1997) Proc. Natl. Acad. Sci. USA 94, 2210–2214
2) Yamaguchi, M., Yamazaki, K., Beauchamp, G. K., Bard, J., Thomas, L. & Boyse, E. A. (1981) Proc. Natl. Acad. Sci. USA 78, 5817–5820
3) Bard, J., Yamazaki, K., Curran, M., Boyse, E. A. & Beauchamp, G. K. (2000) Immunogenetics. 51, 514–518

What is claimed is:

1. A gas chromatography type of chemical analysis method for estimating a change of body smell with progressive ageing of a living subject over a period of years, which comprises the step of monitoring an amount of at least one volatile organic substance in a body fluid of an experimental animal or a human being;
   wherein said at least one volatile organic substance is selected from the group consisting of volatile organic substances that increase or decrease with ageing; and
   wherein said at least one volatile organic substance is selected from the group consisting of 2-phenylacetamide, indole, phenol, cedrene, and methylbutyric acid.

2. The method according to claim 1, wherein said at least one volatile organic substance is methylbutyric acid.

3. The method according to claim 1, wherein said at least one volatile organic substance is selected from the group consisting of 2-phenylacetamide, indole, phenol, and cedrene.

* * * * *